US00PP20173P2

(12) United States Plant Patent
Zaiger et al.

(10) Patent No.: US PP20,173 P2
(45) Date of Patent: Jul. 7, 2009

(54) **INTERSPECIFIC *PRUNUS* TREE NAMED 'COPAROSE'**

(50) Latin Name: *Prunus species*
Varietal Denomination: Coparose

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 6 days.

(21) Appl. No.: 12/011,004

(22) Filed: Jan. 24, 2008

(51) Int. Cl.
*A01H 5/00* (2006.01)

(52) U.S. Cl. ..... Plt./180

(58) Field of Classification Search ..... Plt./180
See application file for complete search history.

*Primary Examiner*—Susan B McCormick Ewoldt

(57) ABSTRACT

A new and distinct variety of interspecific *Prunus* tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Fruit with very good flavor and eating quality.
3. Fruit with an attractive dark red skin color.
4. Heavy and regular bearer of fruit.
5. Fruit with good handling and shipping quality.

1 Drawing Sheet

Botanical classification: *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, almonds, cherries and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of plums and interspecific trees, which are known to us, and mentioned herein, are plums 'Royal Zee' (U.S. Plant Pat. No. 5,486), 'Laroda' (non-patented), 'Queen Ann' (non-patented) 'Queen Rosa' (non-patented) and 'Crimson Heart' Interspecific (U.S. Plant Pat. No. 12,943).

ORIGIN OF THE VARIETY

The new and distinct interspecific tree was originated by us from crosses between the following species [*Prunus salicina* and (*Prunus salicina*×*Prunus armeniaca*)]. The present variety was selected from a cross between the proprietary selected seedling '276LF278' and 'Crimson Heart' Interspecific (U.S. Plant Pat. No. 12,943). The seed parent (276LF278) was developed by us from multiple crosses between the following varieties; 'Royal Zee' Plum (U.S. Plant Pat. No. 5,486), 'Laroda' Plum (non-patented), 'Queen Ann' Plum (non-patented) and 'Queen Rosa' Plum (non-patented). We budded a large number of these seedlings to older 'Nemaguard' Rootstock (non-patented) trees to induce earlier fruit production for evaluation. Under close and careful observation, one seedling, which is the present variety exhibited desirable fruit and tree characteristics, was selected in 2003 for additional asexual propagation and commercialization.

ASEXUAL REPRODUCTION OF THE VARIETY

Additional asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which includes plums and plumcots in its parentage is of large size, vigorous upright growth and a productive and regular bearer of medium size, yellow flesh fruit with very good flavor and eating quality. The fruit is further characterized by having firm flesh, holding firm on the tree for 10 days after maturity (shipping ripe), and having good storage and shipping quality. In comparison to the seed parent '276LF278', the new interspecific variety matures in the same maturity time, has an attractive red skin color, compared to a yellow green skin color and has more desirable eating quality with less acidity. In comparison to the 'Royal Zee' Plum (U.S. Plant Pat. No. 5,486), the new variety has larger fruit and is 10 days later in maturity. In comparison to its interspecific pollen parent Crimson Heart (U.S. Plant Pat. No. 12,943), the new variety has yellow flesh, compared to red and is approximately one month later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height for economical harvesting of fruit. Average width 3 meters, varies with cultural practices.

*Vigor.*—Vigorous, growth of 1.5 to 2 meters the first growing season, varies with type and fertility of soil, climatic conditions and cultural practices.

*Form.*—Upright, usually pruned to vase shape to allow more sunlight to center of tree to enhance fruit color and health of fruit spurs.

*Branching habit.*—Upright, crotch angle approximately 30°, increases with crop load.

*Productivity.*—Productive, thinning and spacing of fruit necessary for desired market size.

*Bearer.*—Regular, adequate fruit set 4 consecutive years. No alternate bearing observed.

*Fertility.*—Self sterile, pollinators required.

*Density.*—Medium dense, controlled by pruning.

*Hardiness.*—Hardy in all stone fruit growing areas of California. Tree grown in USDA Hardiness Zone 9. Winter chilling requirement approximately 750 hours at or below 45° F.

Trunk:

*Size.*—Medium to large. Average circumference 45.5 cm at 20.5 cm above ground on 6 year old tree.

*Stocky.*—Medium stocky.

*Texture.*—Medium shaggy, increases with age of tree.

*Color.*—Varies from 10YR 2/2 to 10YR 4/2.

Branches:

*Size.*—Medium. Average circumference 16.1 cm at 1 meter above ground. Crotch angle approximately 30°, increases with heavy crop load.

*Surface texture.*—New growth relatively smooth. Mature growth medium rough, roughness increases with age.

*Lenticels.*—Size— medium. Average number 34 in a 25.8 sq cm section. Average length 3.4 mm. Average width 1.4 mm. Color varies from 7.5YR 4/8 to 7.5YR 5/10.

*Color.*—New growth varies from 5GY 5/8 to 7.5YR 5/6. Mature growth varies from 7.5YR 3/4 to 7.5YR 2/4, varies with age of growth.

Leaves:

*Size.*—Medium. Average length 90.0 mm. Average width 38.9 mm.

*Form.*—Oblanceolate.

*Apex.*—Acuminate.

*Margin.*—Serrulate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Small to medium. Average length 11.8 mm. Average width 1.6 mm. Longitudinally grooved. Surface— glabrous. Color varies from 2.5GY 6/6 to 5GY 6/6.

*Glands.*—Type— globose. Size— small. Average length 0.7 mm. Average diameter 0.6 mm. Average number 4, varies from 2 to 5. Located on base of leaf blade and upper portion of petiole. Color varies from 2.5GY 6/6 to 5GY 6/6.

*Color.*—Upper surface varies from 5GY 4/6 to 5GY 3/6. Lower surface varies from 5GY 5/4 to 5GY 4/4. Midvein color varies from 2.5GY 8/6 to 5GY 7/6.

Flower bud:

*Size.*—Small to medium. Average length 7.8 mm. Average diameter 4.8 mm.

*Hardiness.*—Hardy with respect to California winters.

*Form.*—Conical, becoming elongated just before opening.

*Pedicel.*—Medium. Average length 8.0 mm. Average width 0.6 mm. Color varies from 2.5GY 6/6 to 2.5GY 6/10. Surface— glabrous.

*Color.*—N 9.5/ (white).

*Number of buds per spur.*—Average 13, varies from 9 to 17.

Flowers:

*Blooming period.*—Date of First Bloom Feb. 28, 2007. Date of Petal Fall Mar. 7, 2007, varies slightly with climatic conditions.

*Size.*—Medium. Average height 12.6 mm. Average diameter 18.4 mm.

*Petals.*—Number 5, alternately arranged to sepals. Size— medium. Average length 10.0 mm. Average width 7.7 mm. Form varies from globose to slightly elongated. Margin— sinuate. Color— N 9.5/ (white). Both upper and lower surfaces glabrous.

*Sepals.*—Number 5, alternately arranged to petals. Shape— triangular, apex rounded. Size— small. Average length 3.2 mm. Average width 2.5 mm. Both upper and lower surfaces glabrous. Margin entire. Color— upper surface varies from 5GY 6/6 to 7.5GY 6/6. Lower surface varies from 5GY 6/6 to 5GY 6/8.

*Stamens.*—Average number 31. Average filament length 9.9 mm. Filament color N 9.5/ (white). Anther color varies from 5Y 8/8 to 5Y 8/10.

*Pollen.*—Present, self sterile, pollinator required. Color varies from 5Y 7/8 to 5Y 7/10.

*Pistil.*—Normally one. Surface— glabrous. Average length 8.1 mm. Position of stigma average of 0.7 mm below anthers. Color varies from 10Y 8.5/6 to 10Y 8/6.

*Fragrance.*—Moderate aroma.

*Color.*—N 9.5/ (white).

*Number flowers per flower bud.*—Average 3, varies from 1 to 4.

*Pedicel.*—Average length 9.8 mm. Average width 0.6 mm. Color varies from 2.5GY 6/6 to 2.5GY 6/8. Surface— glabrous.

Fruit:

*Maturity when described.*—Firm ripe.

*Date of first picking.*—Jul. 1, 2007.

*Date of last picking.*—Jul. 9, 2007, varies slightly with climatic conditions.

*Size.*—Medium. Average diameter axially 49.1 mm. Average transversely in suture plane 62.1 mm. Average weight 125.0 grams, varies slightly with fertility of the soil, amount of thinning and climatic conditions.

*Form.*—Oblate.

*Suture.*—Nearly smooth, extends from base to apex.

*Ventral surface.*—Nearly smooth.

*Apex.*—Nearly flat to very slightly retuse.

*Base.*—Flat to slightly retuse.

*Cavity.*—Rounded to slightly elongated in suture plane. Average depth 4.8 mm. Average diameter 5.8 mm.

Stem:

*Size.*—Small. Average length 11.6 mm. Average diameter 1.7 mm.

*Color.*—Varies from 2.5GY 7/6 to 2.5GY 5/8.

Flesh:

*Ripens.*—Slightly earlier near skin surface.

*Texture.*—Firm, meaty.

*Fibers.*—Few, small, tender.

*Firmness.*—Firm, similar to firmness of 'Laroda' Plum (non-patented).

*Aroma.*—Slight.

*Amydgalin.*—Undetected.

*Eating quality.*—Very good.

*Flavor.*—Very good, good balance between acid and sugar.

*Juice.*—Moderate amount, enhances flavor.

*Brix.*—Average 15°, varies slightly with amount of fruit per tree and climatic conditions.

*Color.*—Varies from 2.5Y 9/2 to 5R 7/6. Pit cavity varies from 2.5Y 7/6 to 2.5Y 6/6.

Skin:

*Thickness.*—Medium.

*Surface.*—Smooth.

*Bloom.*—Moderate amount, complete coverage.

*Tendency to crack.*—None.

*Color.*—Ground color varies from 10Y 8/4 to 10Y 8/6. Overspread with 5R 3/10 to 5R 2/4.

*Tenacity.*—Tenacious to flesh.

*Astringency.*—Undetected.

Stone:

*Type.*—Clingstone.

*Size.*—Small to medium. Average length 22.3 mm. Average width 18.5 mm. Average thickness 13.1 mm.

*Form.*—Obovoid.

*Base.*—Relatively flat, varies from flat to rounded.

*Apex.*—Pointed. Average length 1.7 mm.

*Surface.*—Pitted throughout.

*Sides.*—Unequal, one side extending further from suture plane.

*Ridges.*—Small, narrow ridges extending from base to apex.

*Tendency to split.*—None.

*Color.*—Varies from 10YR 6/8 to 10YR 5/8.

Kernel:

*Size.*—Small to medium. Average length 13.1 mm. Average width 11.0 mm. Average thickness 6.9 mm.

*Form.*—Ovate.

*Viability.*—Viable, embryo fully developed.

*Skin.*—Color varies from 5Y 9/4 to 7.5Y 9/4.

Use: Dessert.

*Market.*—Local and long distance.

Keeping quality: Good, held firm in cold storage for 2 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of medium size, clingstone fruit with very good flavor and eating quality; the fruit is further characterized by having firm flesh, good shipping and storage quality and in comparison to the 'Royal Zee' Plum (U.S. Plant Pat. No. 5,486) the new variety has larger fruit and is 10 days later in maturity.

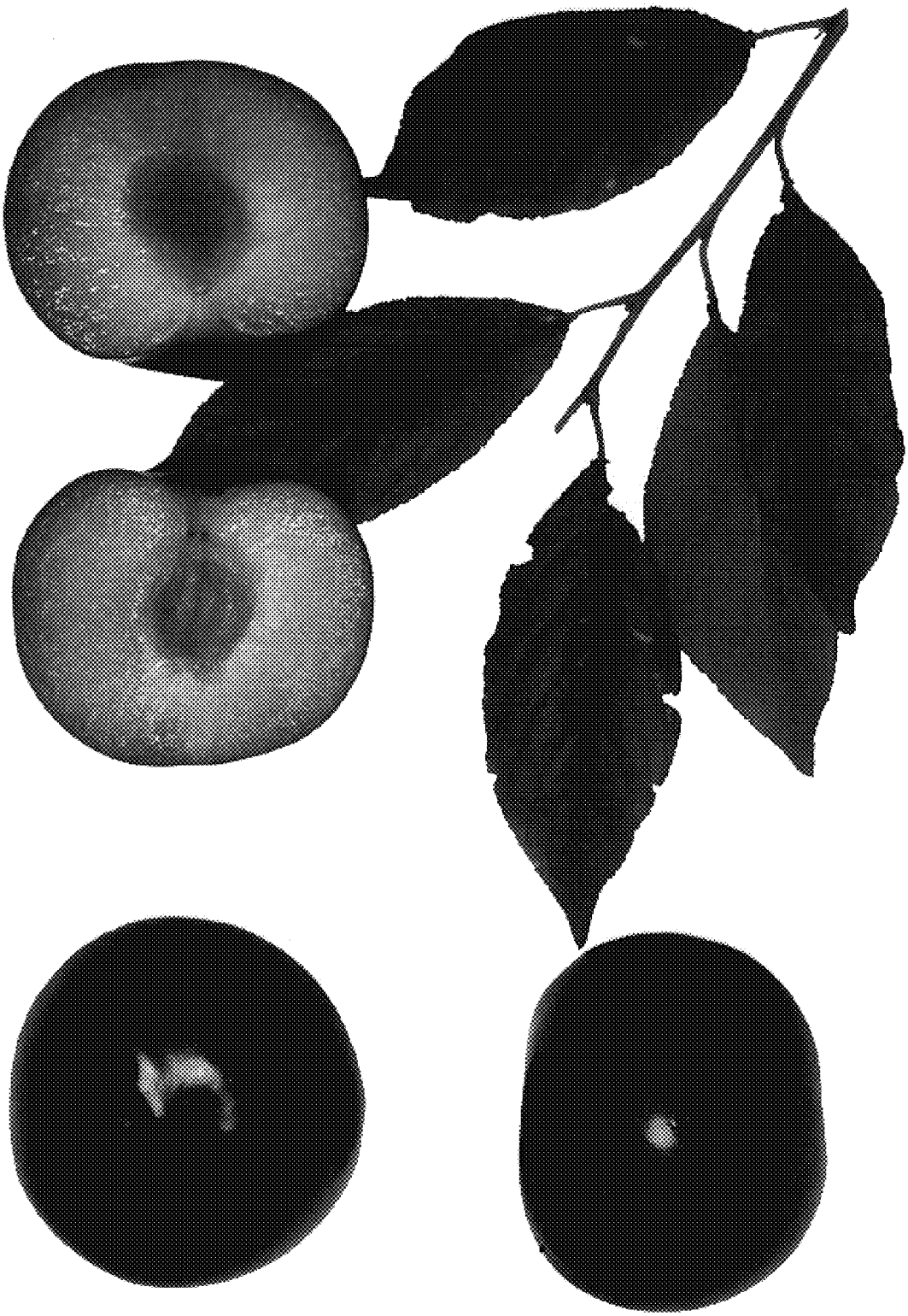

* * * * *